United States Patent [19]

Massie

[11] 3,969,413
[45] July 13, 1976

[54] HYDROFORMYLATION PROCESS USING CATALYST COMPRISING COBALT AND POLYNITROARYL COMPOUNDS

[75] Inventor: Stephen N. Massie, Palatine, Ill.

[73] Assignee: Universal Oil Products Company, Des Plaines, Ill.

[22] Filed: Jan. 20, 1975

[21] Appl. No.: 542,739

[52] U.S. Cl. ............... 260/604 HF; 260/598; 260/602; 260/615 R; 260/617 M; 260/617 HF; 260/633
[51] Int. Cl.² .................................. C07C 27/22
[58] Field of Search ............... 260/632 HF, 604 HF

[56] References Cited
UNITED STATES PATENTS

| | | | |
|---|---|---|---|
| 3,231,621 | 1/1966 | Slaugh | 260/632 HF |
| 3,239,570 | 3/1966 | Slaugh et al. | 260/632 HF |
| 3,369,050 | 2/1968 | Greene | 260/632 HF |
| 3,839,471 | 10/1974 | Wilkes | 260/632 HF |

*Primary Examiner*—Joseph E. Evans
*Attorney, Agent, or Firm*—James R. Hoatson, Jr.; Raymond H. Nelson; William H. Page II

[57] ABSTRACT

A hydroformylation process comprising the treatment of an unsaturated compound with carbon monoxide and hydrogen in the presence of a catalyst comprising a polynitroaromatic and a cobalt-containing compound is disclosed.

17 Claims, No Drawings

HYDROFORMYLATION PROCESS USING CATALYST COMPRISING COBALT AND POLYNITROARYL COMPOUNDS

This invention relates to a process for the preparation of alcohols and aldehydes from the treatment of unsaturated compounds. More specifically, this invention relates to a process for the production of alcohols and aldehydes which comprises the treatment of an unsaturated compound with carbon monoxide and hydrogen in the presence of a catalyst comprising a polynitroaromatic and a cobalt-containing compound.

Processes directed to the production of reaction mixtures comprising substantial amounts of aldehydes and alcohols by the hydroformylation of unsaturated compounds with carbon monoxide and hydrogen in the presence of certain catalysts are well known in the art. The aldehydes and alcohols produced generally correspond to the compounds obtained by the addition of a carbonyl or carbinol group to an olefinically unsaturated carbon atom in the starting material with simultaneous saturation of the olefin bond. The process is known as hydroformylation and involves a reaction which may be shown by the general generic formula:

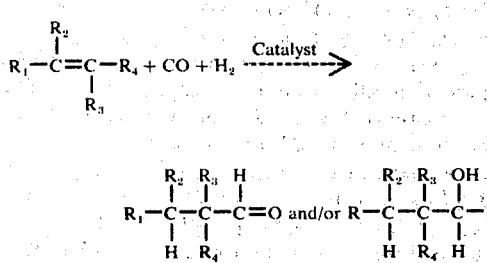

wherein $R_1$, $R_2$, $R_3$ and $R_4$ may be chosen from a group comprising an organic, halide or hydrogen radical.

It has been shown in the prior art that dicobalt octacarbonyl has generally been used as a catalyst for the hydroformylation of unsaturated compounds. This catalyst, which can be prepared from many forms of cobalt, usually decomposes rapidly at elevated temperatures unless high pressures of about 200–4500 pounds per square inch gauge of carbon monoxide are maintained, depending on the temperature. Correspondingly, high pressures of hydrogen are also necessary. Another serious disadvantage of hydroformylation processes has been the necessity of proceeding in two steps when alcohols are the desired products. Another disadvantage inherent in the hydroformylation process is the relative inability to direct the reactions involved to the production of predominantly terminal alcohols when the olefins contain more than 2 carbon atoms, particularly when the charge stock to the process comprises primarily internal olefins. Still another and more basic problem in a hydroformylation reaction is the production of heavy byproduct formations which are worthless and create a disposal problem. Still another byproduct problem is the production of alkane compounds, which are also worthless byproducts of hydroformylation reactions.

In contradistinction to the prior art, it has now been shown that the utilization of the catalyst comprising a polynitroaromatic and a cobalt-containing compound during the hydroformylation of an unsaturated compound by carbon monoxide and hydrogen will add a different dimension to the basic hydroformylation process. The utilization of the present invention will allow the manufacturer an advantage in the production of aldehydes and alcohols as a result of the decrease in heavy byproducts normally present in known hydroformylation processes. The decrease in hydroformylation heavy byproducts will consequently ease any heavy byproduct disposal problems of the manufactuer. Further, the presence of the novel catalyst will decrease the total quantity of byproducts normally produced in known hydroformylation reactions of unsaturated compounds. Further, the decrease of the heavy byproducts will not decrease the percentage of aldehydes and alcohols prepared by hydroformylation of the unsaturated compounds. I have found that the utilization of this novel catalyst will not only decrease the quantity of heavy byproducts but also increase the quantity of hydroformylation products, namely, aldehydes and alcohols. The utilization of this invention will also permit the manufacturer to perform an efficient hydroformylation process without any excess problems of alkane formation.

The desired products to the process of this invention, namely alcohols and aldehydes, are utilized in the chemical industry in many ways. For example, alcohols are utilized in the synthesis of other organic derivatives; as solvents; as an extraction medium; in dyes; synthetic drugs; synthetic rubber; detergents; cleaning solutions; surface coatings; cosmetics; pharmaceuticals; in the preparation of esters; as a solvent for resin in coatings; as a plasticizer; dyeing assistant; hydraulic fluids; detergent formulations; dehydrating agents; or the use of aldehydes as exemplified by their utility as perfumeries, or in the synthesis of primary alcohols.

It is therefore an object of this invention to provide a process for the preparation of hydroformylation products, namely, aldehydes and alcohols.

A further object of this invention is to provide an improvement in a process for the preparation of hydroformylation products utilizing certain catalytic compositions of matter which will permit the recovery of the desired compounds in a more economically feasible manner.

In one aspect an embodiment of this invention resides in a process for the preparation of hydroformylation products which comprises hydroformylating an unsaturated compound with carbon monoxide and hydrogen in the presence of a catalyst comprising a polynitroaromatic and a cobalt-containing compound at reaction conditions, and recovering the resultant hydroformylated product.

A specific embodiment of this invention resides in a process for preparing undecanol-1 which comprises hydroformylating decene-5 with carbon monoxide and hydrogen in the presence of a catalyst comprising dicobalt octacarbonyl and 2,4,6-trinitrotoluene at a temperature of 195° C. and a pressure of 80 atmospheres of hydrogen and 20 atmospheres of carbon monoxide, said catalytic components comprising dicobalt octacarbonyl and 2,4,6-trinitrotoluene in an equimolar ratio and recovering the resultant undecanols.

Another specific embodiment of this invention resides in a process for preparing a mixture of dodecanol-1, 2-methylundecanol-1, 2-ethyldodecanol-1, 2-propylnonanol-1, tridecanol-1, 2-methyldodecanol-1, 2-ethylundecanol-1, tetradecanol-1, 2-methyltridecanol-1, 2-ethyldodecanol-1, pentadecanol-1, 2-methyltetradecanol-1, and 2-ethyltridecanol-1 which comprises the mixture of undecene-5, dodecene-4, -tridecene-6 and tetradecene-4 in the presence of a catalyst comprising dicobalt octacarbonyl and 2, 4-dinitrophenylhydrazine, said catalytic components being present in equimolar proportions at a temperature of 150° C. and a pressure of 100 atmospheres of hydrogen and 50 atmospheres of carbon monoxide and recovering the resultant mixture comprising dodecanol-1, 2-methylundecanol-1, 2-ethyldodecanol-1, 2-propylnonanol-1, tridecanol-1, 2-methyldodecanol-1, 2-ethylundecanol-1, tetradecanol-1, 2-methyltridecanol-1, 2-ethyldodecanol-1, pentadecanol-1, 2-methyltetradecanol-1, and 2-ethyltridecanol-1.

Other objects and embodiments will be found in the following further detailed description of the present invention.

As hereinbefore set forth the present invention is concerned with a process for preparing hydroformylation products, namely, alcohols and aldehydes, said process being effected by the hydroformylation of an unsaturated compound with carbon monoxide and hydrogen in the presence of a catalyst comprising a polynitroaromatic and cobalt-containing compound. The reaction is effected under conditions which include a temperature in the range of from about 75° C. to about 300° C. and preferably in a range of from about 100° C. to about 200° C. In addition, another reaction condition involves pressure, said pressure ranging from about 20 atmospheres up to 500 atmospheres or more. The superatmospheric pressures which are employed are afforded by the introduction of gaseous carbon monoxide, hydrogen and, if desired, any substantially inert gas such as nitrogen or helium may also be charged to the reaction zone. Another reaction variable which is employed is the proportional amounts of the components of the catalyst system present in the hydroformylation process. It is contemplated within the scope of this invention that the polynitroaromatic component of the catalyst system be present in a molar ratio of from about three moles of the polynitroaromatic compound to about one-half mol of the polynitroamomatic compound per gram-atom of cobalt in the cobalt-containing compound component of the catalyst system. It is also contemplated that the molar proportion be greater than three or less than one, although this would not be deemed economically advantageous.

Examples of suitable unsaturated compounds which are utilized as the starting material in the hydroformylation process of this invention include, in particular, olefins possessing from 3 to 20 carbon atoms, alkyl, alkoxy or halo substituted olefins possessing from 3 to 20 carbon atoms, cycloolefins possessing from about 5 to 10 carbon atoms or alkyl, alkoxy or halo substituted cycloolefins possessing from 5 to 10 carbon atoms such as propylene, butene-1, butene-2, isobutene, pentene-1, pentene-2, 2-methylbutene-1, 2-methylbutene-2, hexene-1, 3-methylpentene-1, 2-methylpentene-2, heptene-2, 2-methylhexene-2, 3-methylhexene-2, octene-1, octene-2, 3-methylheptene-1, 2-methylheptene-2, nonene-3, 3-methyloctene-2, decene-2, decene-5, 3, 4-dimethyloctene-2, 4-ethyloctene-2, undecene-3, undecene-4, 4-methyldecene-2, 4, 5-dimethylnonene-2, dodecene-3, tridecene-2, tetradecene-3, pentadecene-5, heptene-1, nonene-1, decene-1, decene-2, decene-3, decene-4, decene-5, undecene-1, dodecene-2, undecene-2, undecene-3, undecene-4, undecene-5, dodecene-1, dodecene-3, dodecene-5, tridecene-1, tridecene-3, tridecene-4, tridecene-6, tetradecene-1, tetradecene-7, pentadecene-1, pentadecene-4, pentadecene-6, 2-methoxybutene-2, 2-methoxypentene-1, 2-ethoxyhexene-1, 1-propoxyheptane, 2-ethoxyoctene-1, 2, 3-diethoxyundecene-3, 1-chlorobutene-2, 2-chloropentene-1, 2-bromohexene-2, 2, 3-dichlorooctene-1, 3-iodooctene-2, 2-methoxy-3-chlorodecene-2, 3, 4-dimethyl-2-chlorooctene-2, cyclopentene, cyclohexene, cycloheptene, cyclooctene, cyclononene, cyclodecene, 1-methylcyclohexene-1, 1-ethylcyclohexene-1, 2, 3-dipropylcycloheptene-1, 1-methoxycyclopentene-1, 2, 3-dipropylcycloheptene-1, 1-chlorocycloheptene-1, 2, 3, 4-trichlorocyclooctene-1, or mixtures of linear internal olefins such as internal olefins possessing carbon numbers of 8 through 10, 11 through 14 or 15 through 18, etc.

It is contemplated within the scope of the process of the present invention that the hydroformyltion may be effected in an inert organic media as exemplified by n-pentane, n-hexane, n-heptane, n-octane, n-nonane, isooctane (2, 2, 4-trimethylpentane), cyclohexane, methylcyclohexane, benzene, toluene, etc.

The catalytic system of the present invention comprises two components, one being a polynitroaromatic compound and the second a cobalt-containing compound. The catalyst system may be present in the hydroformylation reaction in a range of about 0.001 mols of catalyst system to about 0.05 mols of the catalyst system per mol of the unsaturated compound. The polynitroaromatic compound may be exemplified by any aromatic or lower alkyl, amino, alkoxy, halo, hydroxy or carboxy substituted aromatic compound which is substituted with two or more nitro radicals ($NO_2$). Suitable examples would include 2,4-dinitrotoluene, 2,3-dinitrotoluene. 3,5-dinitrotoluene, 2,3,4-trinitrotoluene, 2,3,5-trinitrotoluene, 3,4,5-trinitrotoluene, 2,4,6-trinitrotoluene, 2,3,4,5-tetranitrotoluene, 2,4-dinitrocumene, 2,3-dinitrocumene, 3,5-dinitrocumene, 2,3,4-trinitrocumene, 2,3,5-trinitrocumene, 3,4,5-trinitrocumene, 2,4,6-trinitrocumene, 2,3,4,5-tetranitrocumene, 2,4-dinitrobenzene, 2,3-dinitrobenzene, 3,5-dinitrobenzene, 2,3,4-trinitrobenzene, 2,3,5-trinitrobenzene, 3,4,5-trinitrobenzene, 2,4,6-trinitrobenzene, 2,3,4,5-tetranitrobenzene, 2,4-dinitroaniline, 2,3-dinitroaniline, 3,5-dinitroaniline, 2,3,4-trinitroaniline, 2,3,5-trinitroaniline, 3,4,5-trinitroaniline, 2,4,6-trinitroaniline, 2,3,4,5-tetranitroaniline, 2,4-dinitroanisole, 2,3-dinitroanisole, 3,5-dinitroanisole, 2,3,4-trinitroanisole, 2,3,5-trinitroanisole, 3,4,5-trinitroanisole, 2,4,6-trinitroanisole, 2,3,4,5-tetranitroanisole, 2,4-dinitrochlorobenzene, 2,3-dinitrochlorobenzene, 3,5-dinitrochlorobenzene, 2,3,4-trinitrochlorobenzene, 2,3,5-trinitrochlorobenzene, 3,4,5-trinitrochlorobenzene, 2,4,6-trinitrochlorobenzene, 2,3,4,5-tetranitrochlorobenzene, 2,4-dinitrobromobenzene, 2,3-dinitrobromobenzene, 3,5-dinitrobromobenzene, 2,3,4-trinitrobromobenzene, 2,3,5-trinitrobromobenzene, 3,4,5-trinitrobromobenzene, 2,4,6-trinitrobromobenzene, 2,3,4,5-tetranitrobromobenzene, 2,4-dinitrophenol, 2,3-dinitrophenol, 3,5-dinitrophenol, 2,3,4-trinitrophenol, 2,3,5-trinitrophenol, 3,4,5-trinitrophenol, 2,4,6-trinitrophenol, 2,3,4,5-tetranitrophenol, 2,4-dinitrobenzoic acid, 2,3-dinitrobenzoic acid, 3,5-dinitrobenzoic acid, 2,3,4-trinitrobenzoic acid, 2,3,5-trinitrobenzoic acid, 3,4,5-trinitrobenzoic acid, 2,4,6-trinitrobenzoic acid, 2,3,4,5-tetranitrobenzoic acid, etc., and all other compounds which are polynitroaromatic substituted such as hydrazines (2,4- dinitrophenylhydrazine), ethers (2,3-dinitrophenetole) or esters, etc.

Due to the detonation characteristics of many of the polynitroaromatic compounds, reaction residues containing the metallic catalyst and the polynitroaromatic compounds should be treated carefully. Such polynitroaromatic compounds should be removed from the product mixture prior to recovery of aldehydes and alcohols by fractionation.

The second catalytic component will comprise any cobalt-containing catalyst such as dicobalt octacarbonyl. It is also contemplated within the scope of this invention that a phosphorus containing ligand such as a trialkyl phosphine may be present as one component of the complex cobalt catalyst. The hydrocarbonyl components need not necessarily be the same, and suitable tertiary organophosphine ligands comprise the mixed phosphine wherein different members of the group are comprised of alkyls, aryls, aralkyls, and alkaryls. Preferred catalysts of the above-defined class comprise those wherein the hydrocarbonyl component contains from about 1 to about 20 carbon atoms and the total number of carbons in the tertiary organo phosphine group does exceed about 30. A particularly preferred group of catalysts within the above-defined trialkyl phosphine-cobalt carbonyl complexes is one in which the component of the catalyst is a trialkylphosphine in which each alkyl is a lower alkyl having from 1 to about 10 carbon atoms. Specific examples of suitable catalysts of the above-defined class comprise complexes between cobalt, carbon monoxide and one of the following tertiary organophosphines such as trimethylphosphine, triethylphosphine, tris-n-butylphosphine, triamylphosphine, trihexylphosphine, tripropylphosphine, trinonylphosphine, tridecylphosphine, tri-n-butyloctadecylphosphine, dimethylethylphosphine, diamylethylphosphine, ethyl-bis-($\beta$-phenylethyl)phosphine, dimethylcyclopentylphosphine, diphenylbenzylphosphine, diethylphenylphosphine, etc. It should be noted that the presence of the organophosphine is not critical to the above set forth invention and that the polynitroaromatic compound can function in the sole presence of the cobalt-containing compound. It is also within the scope of this invention to charge a cobalt-containing compound which will generate dicobalt octacarbonyl or hydridocobalt tetracarbonyl under the reaction conditions, said compounds being exemplified by cobalt carbonate, cobalt octanate, cobalt naphthenate, cobalt chloride, etc.

It is understood that the aforementioned polynitroaromatic compounds, cobalt-containing compounds, unsaturated compounds and inert organic mediums are only representative of the class of compounds which may be employed, and that the present invention is not necessarily limited thereto.

The process of this invention may be effected in any suitable manner and may comprise either a batch or continuous type operation. For example, when a batch type operation is employed the reactants comprising the unsaturated compounds, carbon monoxide and hydrogen are placed in an appropriate apparatus along with a catalyst comprising a cobalt-containing compound and a polynitroaromatic compound. The autoclave is sealed, heated to a desired operating temperature and maintained thereat for a predetermined residence time. At the end of this time, which may comprise from 0.5 up to 50 hours or more in duration, the heating is discontinued, the autoclave is allowed to return to room temperature and the autoclave is vented thereby allowing it to return to ambient pressure. The reaction mixture is then recovered, separated from the catalyst system and subjected to conventional means of purification and separation, said means include washing, drying, extraction, evaporation, fractional distillation, etc., where the desired hydroformylation products, namely, alcohols, aldehydes or alcohol-aldehyde mixtures are recovered.

It is also contemplated within the scope of this invention that the hydroformylation process for obtaining the desired alcohols and aldehydes will be effected in a continuous manner of operation. When such a type of operation is employed, the reactants comprising the unsaturated compounds are continuously charged to a hydroformylation zone containing a catalyst system comprising a cobalt-containing compound and a polynitroaromatic compound, said hydroformylation zone being maintained at proper operating conditions of pressure and temperature by heat and the admission of requisite amounts of carbon monoxide and hydrogen and any substantially inert gas desired for effecting the hydroformylation reaction. After completion of the desired residence time, the reactor effluent is continuously withdrawn and subjected to conventional means of separation whereby the desired alcohols, aldehydes or alcohol-aldehyde mixtures are recovered while any unreacted starting material comprising the unsaturated compound, carbon monoxide and hydrogen are recycled to the reaction zone to form a portion of the feedstock or gaseous hydrogen or carbon monoxide stream. The cobalt values or the polynitroaromatic compounds may be recovered from the reaction mixture by various recovery methods known to the art and regenerated to form a viable catalyst system.

Examples of alcohols and aldehydes which may be prepared according to the process of this invention will include butanol-1, pentanol-1, hexanol-1, heptanol-1, octanol-1, nonanol-1, decanol-1, 2-methylbutanol-1, 2-methylpentanol-1, 2-ethylpentanol-1, 2-methylhexanol-1, 2-ethylhexanol-1, 2-chloropropanol-1, 3-chlorohexanol-1, 2, 3-dichloroheptanol-1, 2-ethyl-3-chlorooctanol-1, butanal, pentanal, hexanal, heptanal, octanal, nonanal, decanal, undecanal, 2-methylbutanal, 2-methyloctanal, cyclopentyl carbinol, cyclohexyl carbinol, cycloheptyl carbinol, cyclooctyl carbinol, cyclononyl carbinol, cyclodecyl carbinol, mixed hydroxymethylalkanes, mixed formylalkanes, etc.

The following examples are given to illustrate the process of the present invention which, however, are not intended to limit the generally broad scope of the present invention in strict accordance therewith.

EXAMPLE I

In this example 20.0 grams of decene-5 was added to an 850 ml rotating autoclave which was flushed with nitrogen and subsequently stoppered. Immediately prior to sealing the autoclave, a solution of 1 mmole of cobalt as dicobalt octacarbonyl in 5 ml of n-pentane was charged to the autoclave by means of a syringe. Carbon monoxide was charged to an initial carbon monoxide pressure of 20 atmospheres and hydrogen was charged to an initial pressure of 80 atmospheres, said total pressure being 100 atmospheres. The autoclave was heated to a temperature of 150° C. and maintained thereat for a period of time comprising 8 hours. After passage of the 8-hour period of time, the autoclave was stopped, allowed to return to room temperature after the termination of heat, vented in a fume hood and flushed with nitrogen to remove any residual carbon monoxide. The reaction product was recovered from the autoclave and analyzed by means of gas-liquid chromatography instrumentation, said analysis disclosed the following properties set forth in Table I below.

TABLE I

| | |
|---|---|
| n-decane, wt. % | 5.4 |
| undecanal, wt. % | 1.0 |
| other branched-chain isomers of aldehydes, wt. % | 1.5 |
| undecanol-1 wt. % | 28.0 |
| isomers of undecanol-1 wt. % | 35.3 |
| heavy elutable byproducts, wt. % | 15.7 |
| non-elutable byproducts, wt. % (by difference) | 6.9 |
| sum of alcohol and aldehyde, wt. % | 67.0 |
| total byproducts | 22.6 |
| total decene-5 conversion | 99.0 |

The experiment was repeated with identical physical parameters, the results being set forth in Table II below.

TABLE II

| | |
|---|---|
| n-decane, wt. % | 5.9 |
| undecanal, wt. % | 2.1 |
| other branched-chain isomers of aldehydes, wt. % | 4.5 |
| undecanol-1 wt. % | 26.1 |
| isomers of undecanol-1 wt. % | 31.6 |
| heavy elutable byproducts, wt. % | 22.1 |
| non-elutable byproducts | 1.0 |
| sum of alcohol and aldehyde, wt. % | 65.3 |
| total byproducts | 23.1 |
| total decene-5 conversion | 99.0 |

EXAMPLE II

In this example 20.0 grams of decane-5 and 1 mmole of 2,4,6-trinitrotoluene were added to an 850 ml rotating autoclave which was flushed with a nitrogen purge and stoppered. Immediately prior to sealing the autoclave, a solution of 1 mmole of cobalt as dicobalt octacarbonyl in 5 ml of n-pentane was charged to the autoclave by means of a syringe. Carbon monoxide was charged to an initial carbon monoxide pressure of 20 atmospheres and hydrogen was charged to an initial pressure of 80 atmospheres, said total initial pressure being 100 atmospheres. The autoclave was heated to a temperature of 150° C. and maintained thereat for a period of time comprising 8 hours. After passage of the 8-hour period of time, the autoclave was stopped, allowed to return to room temperature after the termination of heat, vented in a fume hood and flushed with nitrogen to remove any residual carbon monoxide. The reaction product was recovered from the autoclave and analyzed by means of gas-liquid chromatography instrumentation, said analysis disclosed the following properties set forth in Table III below.

TABLE III

| | |
|---|---|
| n-decane, wt. % | 4.4 |
| undecanal, wt. % | 0.5 |
| other branched-chain isomers of aldehydes, wt. % | Trace |
| undecanol-1 wt. % | 27.5 |
| isomers of undecanol-1 wt. % | 40.5 |
| heavy elutable byproducts, wt. % | 10.7 |
| non-elutable byproducts | 9.9 |
| sum of alcohol and aldehyde, wt. % | 69.3 |
| total byproducts | 20.6 |
| total decene-5 conversion | 100.0 |

It can be seen from a comparison of Table III with Tables I or II that the presence of the polynitroaromatic (2,4,6-trinitrotoluene) enhanced the production of desired hydroformylation products and decreased the total amount of heavy byproducts. In Table III, 20.6 weight percent heavy byproducts were produced in comparison with 22.6 weight percent byproducts of Table I and 23.1 weight percent byproducts of Table II. The amount of undesirable heavy byproducts was reduced from 2.0 weight percent to 2.5 weight percent by the presence of the catalyst comprising the polynitroaromatic compound, namely, 2,4,6-trinitrotoluene. Even though the amount of byproducts was reduced, the total amount of hydroformylated products was increased, said hydroformylation products will comprise alcohols and aldehydes. The quantity of alcohols plus aldehydes was increased from 65.3 and 67.0 weight percent of Tables II and I respectively to 69.3 weight percent of Table III. The presence of catalyst comprising the polynitroaromatic compound, namely, 2,4,6-trinitrotoluene, increased the production of hydroformylated products from 2.3 weight percent to 4.0 weight percent.

EXAMPLE III

In this example 142.0 mmoles of decene-5 and 2 mmoles of 2,4,6-trinitrotoluene were added to an 850 ml rotating autoclave which was flushed with a nitrogen purge and stoppered. Immediately prior to sealing the autoclave, a solution of 1 mmole of dicobalt octacarbonyl dissolved in 5 ml of n-pentane was charged by means of a syringe. Carbon monoxide was charged to an initial carbon monoxide pressure of 20 atmospheres and hydrogen was charged to an initial hydrogen pressure of 80 atmospheres, said total initial pressure being 100 atmospheres. The autoclave was heated to a temperature of 150° C. and maintained thereat for a period of time comprising 8 hours during continual rotation. After the passage of the 8 hours of time the autoclave was stopped, allowed to return to room temperature after the termination of heat, vented in a fume hood and flushed with nitrogen to remove any residual carbon monoxide. The reaction product was recovered from the autoclave, separated from the catalyst system and analyzed by means of gas-liquid chromatography, said analysis disclosed the product to contain a decrease in the quantity of total byproducts and an increase in undecanols as compared to an example in which the catalyst comprised only the dicobalt octacarbonyl.

EXAMPLE IV

In this example 143.0 mmoles of decene-5 and 1 mmole of 2,4-dinitrophenylhydrazine was added to an 850 ml rotating autoclave which was flushed with a nitrogen purge and stoppered. Immediately prior to sealing the autoclave, a solution of 1 mmole of dicobalt octacarbonyl dissolved in 5 ml of n-pentane was charged to the autoclave by means of a syringe. Carbon monoxide was charged to an initial carbon monoxide pressure of 20 atmospheres and hydrogen was charged to an initial hydrogen pressure of 80 atmospheres, said total initial pressure being 100 atmospheres. The autoclave was heated to a temperature of 150° C. and maintained thereat for a period of time comprising 8 hours during continual rotation. After the passage of the 8 hours of time the autoclave was stopped, allowed to return to room temperature after the termination of heat, vented in a fume hood and flushed with nitrogen to remove any residual carbon monoxide. The reaction product was recovered from the autoclave, separated from the catalyst system and analyzed by means of gas-liquid chromatography, said analysis disclosed the product to contain a decrease in the quantity of total byproducts and an increase in undecanols as compared to an example in which the catalyst comprised only the dicobalt octacarbonyl.

EXAMPLE V

In this example the experiment of Example IV was conducted with the same physical constants with the exception of a change in the addition of 1 mmole of 3,4-dinitrotoluene for the 2,4-dinitrophenylhydrazine. The results of the corresponding gas-liquid chromatography instrumentation analysis disclosed the product to contain a decrease in the quantity of total byproducts and an increase in undecanols as compared to an example in which the catalyst comprised only the dicobalt octacarbonyl.

EXAMPLE VI

In this example the experiment of Example IV was maintained at the exact physical conditions with the exception of a substitution of 1 mmole of trinitrophenol for the 2,4-dinitrotoluene. The gas-liquid chromatography analysis disclosed the product to contain a decrease in the quantity of total byproducts and an increase in the undecanols as compared to an example in which the catalyst comprised only the dicobalt octacarbonyl.

EXAMPLE VII

In this example the experiment of Example IV was maintained at the same physical constants with the exception of the substitution of 1 mmole of 2,4-dinitrophenyl ethyl ether for the 2,4-dinitrophenylhydrazine, said gas-liquid chromatography analysis disclosed the product to contain a decrease in the quantity of total byproducts and an increase in undecanols as compared to an example in which the catalyst comprised only the dicobalt octacarbonyl.

EXAMPLE VIII

In this example 100.0 mmoles of tetradecene-7 are placed in an 850 ml rotating autoclave containing 0.5 mmoles of 2,4,6-trinitrotoluene and 0.5 mmoles of a complex between cobalt, carbon monoxide and diethylphenylphosphine, said autoclave being equipped with a device for heating and pressure attainment. The rotating autoclave is heated to a temperature of 200° C., after being pressurized with 150 atmospheres of hydrogen and 150 atmospheres of carbon monoxide and maintained thereat for a period of time comprising 2 hours. At the end of the 2-hour period of time, the heating is terminated, thereby allowing the rotating autoclave to return to room temperature and the autoclave is vented thereby allowing it to return to ambient pressure. At this point the product is removed from the rotating autoclave and analyzed by means of gas-liquid chromatography instrumentation, said analysis disclosing the product to be a mixture of pentadecanol, 2-methyltetradecanol-1 and 2-ethyltridecanol with a minimum quantity of byproducts.

EXAMPLE IX

In this example the physical conditions of Example VII are repeated with the substitution of 1 mmole of 2,3,4-trinitrocumene for the 2,4,6-trinitrotoluene, said chromatographic analysis discloses the products to be a mixture of pentadecanol, 2-methyltetradecanol-1 and 2-ethyltridecanol with a minimum quantity of byproducts.

EXAMPLE X

In this example the physical conditions of Example VIII are maintained with the substitution of 100.0 mmoles of heptene-3 for the 100.0 mmoles of tetradecene-7, said chromatographic analysis discloses the product to comprise octanol-1 with a minimum quantity of byproducts.

EXAMPLE XI

In this example the physical conditions of Example VIII are maintained with the substitution of 100.0 mmoles of hexadecene-8 and 0.5 mmoles of 2,3-dinitrobenzoic acid for the 2,4,6-trinitrotoluene. The subsequent gas-liquid chromatographic analysis discloses the product to comprise heptadecanals and heptadecanols with a minimum quantity of byproducts.

EXAMPLE XII

In this example 110.0 mmoles of a mixture comprising undecene-5, dodecene-4, tridecene-6 and tetradecene-4 in equimolar proportions are placed in an 850 ml rotating autoclave containing 1.2 mmoles of 2,4,6-trinitroanisole and 0.5 mmoles of a complex between cobalt, carbon monoxide and diethylphenylphosphine. The autoclave is equipped with basic devices for both heating and pressure attainment. The rotating autoclave is heated to a temperature of 100° C. after being pressurized with 200 atmospheres of hydrogen and 200 atmospheres of carbon monoxide. The autoclave is maintained at the hereinbefore set forth physical conditions for a period of time comprising 2 hours. At the end of the 2-hour period of time, the heating is terminated thereby allowing the autoclave to return to room temperature and the autoclave is vented thereby allowing it to return to ambient pressure. The product is removed from the rotating autoclave and analyzed by means of gas-liquid chromatography instrumentation, said analysis disclosing a minimum quantity byproducts and the product to be a mixture comprising dodecanol-1, 2-methylundecanol-1, 2-ethyldodecanol-1, 2-propylnonanol-1, tridecanol-1, 2-methyldodecanol-1, 2-ethylundecanol-1, tetradecanol-1, 2-methyltridecanol-1, 2-ethyldodecanol-1, pentadecanol-1, 2-methyltetradecanol-1, and 2-ethyltridecanol-1.

I claim as my invention:

1. A process for the preparation of hydroformylation products which comprises hydroformylating an olefin possessing from 3 to 20 carbon atoms with carbon monoxide and hydrogen in the presence of a catalyst comprising a polynitroaryl which may be substituted by a lower alkyl, amino, halo, hydroxy, carboxy or hydrazino radical and a cobalt-containing compound at a temperature in the range of about 75° to 300°C and a pressure of 20 atmospheres to 500 atmospheres and recovering the resultant hydroformylation products.

2. The process of claim 1 further characterized in that the polynitroaryl compound is present in a mole ratio of about 1 mole of the polynitroaromatic compound to about 3 moles of the polynitroaromatic compound per mole of the cobalt-containing compound.

3. The process of claim 1 further characterized in that the hydroformylation reaction is effect in an inert organic medium.

4. The process of claim 3 further characterized in that the inert organic reaction medium is n-pentane.

5. The process of claim 3 further characterized in that the inert organic reaction medium is 2,2,4-trimethylpentane.

6. The process of claim 1 further characterized in that the unsaturated compound is decene-5 and the resultant hydroformylation product is undecanol-1.

7. The process of claim 1 further characterized in that the unsaturated compound is tetradecene-7 and the resultant hydroformylation product is pentadecanol-1.

8. The process of claim 1 further characterized in that the unsaturated compound is heptene-3 and the resultant hydroformylation product is octanol-1.

9. The process of claim 1 further characterized in that the unsaturated compound is hexadecene-8 and the resultant hydroformylation product is heptadecanal-1.

10. The process of claim 1 further characterized in that the unsaturated compound is a mixture of internal olefins and the resultant hydroformylation product is a mixture of primary alcohols.

11. The process of claim 10 further characterized in that the mixture of internal olefins comprises undecene-5, dodecene-4, tridecene-6 and tetradecene-4 and the resultant mixture of primary alcohols comprises dodecanol-1, 2-methylundecanol-2, 2-ethyldecanol-1, 2-propylnonanol-1, tridecanol-1, 2-methyltridecanol-1, 2-ethylundecanol-1, tetradecanol-1, 2-methyltridecanol-1, 2-ethyldodecanol-1, pentadecanol-1, 2-methyltetradecanol-1 and 2-ethyltridecanol-1.

12. The process of claim 1 further characterized in that the cobalt-containing compound is dicobalt octacarbonyl.

13. The process of claim 1 further characterized in that the polynitroaryl compound is 2,4,6-trinitrotoluene.

14. The process of claim 1 further characterized in that the polynitroaryl compound is 2,4-dinitrophenylhydrazine.

15. The process of claim 1 further characterized in that the polynitroaryl compound is 2,4-dinitrotoluene.

16. The process of claim 1 futher characterized in that the polynitroaryl compound is 2,3,4-trinitrophenol.

17. The process of claim 1 further characterized in that the polynitroaryl compound is 2,4-dinitrophenyl ethyl ether.

* * * * *